(12) United States Patent
Adler et al.

(10) Patent No.: US 6,505,530 B2
(45) Date of Patent: *Jan. 14, 2003

(54) INK APPLICATION DEVICE FOR TATTOOING OR FOR MAKING PERMANENT MAKE-UP

(75) Inventors: Frank Adler, Berlin (DE); Walter Lisec, Berlin (DE); Gerhard Türk, Berlin (DE)

(73) Assignee: Medium-Tech Medizingeräte GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/072,991

(22) Filed: Feb. 12, 2002

(65) Prior Publication Data

US 2002/0069726 A1 Jun. 13, 2002

Related U.S. Application Data

(63) Continuation of application No. 09/671,650, filed on Sep. 28, 2000, now Pat. No. 6,345,553.

(30) Foreign Application Priority Data

Oct. 22, 1999 (DE) ...................................... 299 19 199 U

(51) Int. Cl.[7] ................................................ B43K 5/00
(52) U.S. Cl. ............................ 81/9.22; 81/438; 30/362; 606/186
(58) Field of Search ..................... 81/9.22, 438; 30/362; 606/186, 169

(56) References Cited

U.S. PATENT DOCUMENTS

| | | |
|---|---|---|
| 4,508,106 A | 4/1985 | Angres |
| 4,644,952 A | 2/1987 | Patipa et al. |
| 4,671,277 A | 6/1987 | Bauchat |
| 4,798,582 A | 1/1989 | Sarath et al. |
| 4,862,772 A | 9/1989 | Piperato |
| 5,279,552 A | 1/1994 | Magnet |
| 5,472,449 A | 12/1995 | Chou |
| 5,586,473 A | 12/1996 | Chou |
| 5,724,873 A | 3/1998 | Hillinger |
| 5,741,290 A * | 4/1998 | Hsieh .......................... 606/186 |
| 6,033,421 A * | 3/2000 | Theiss .......................... 606/186 |

FOREIGN PATENT DOCUMENTS

| | | |
|---|---|---|
| DE | 299 16 971 U1 | 5/2000 |
| GB | 1 587 519 A | 4/1981 |

* cited by examiner

Primary Examiner—James G. Smith
Assistant Examiner—Hadi Shakeri
(74) Attorney, Agent, or Firm—Smith Patent Office

(57) ABSTRACT

An ink application device for tattooing or for making permanent make-up includes a handle, a needle drive, a needle, a needle nozzle and a protective cap. The device further includes at least two modules releasably connected to one another. One of the modules is formed as a reusable base module with an integrated needle drive, and the other module is a sterilized disposable module in which all components of the manual device capable of being infected by bodily fluids of a customer are integrated. The device can be constructively divided into two or three separate modules: a basic module, a disposable or hygienic module and an optional ink module. The basic module corresponds to the handle that includes the needle drive and is designed such that the hygienic module can be safely attached and connected to the integrated needle drive.

20 Claims, 6 Drawing Sheets

INK APPLICATION DEVICE FOR TATTOOING OR FOR MAKING PERMANENT MAKE-UP

BACKGROUND OF THE INVENTION

This application is a continuation application of application Ser. No. 09/671,650 filed on Sep. 28, 2000, now U.S. Pat. No. 6,345,553.

FIELD OF THE INVENTION

The present invention relates to an ink application device for tattooing or for making permanent make-up that can apply tattoos or other permanent make-up. In particular, this invention relates to a permanent make-up ink application device for ensuring sterility when treating customers.

DISCUSSION OF THE RELATED ART

The spreading of highly infectious bacterial or viral infectious diseases such as AIDS and hepatitis, which are transmitted by bodily fluids, places substantial pressure on cosmeticians with respect to the hygienic handling of the tools and ink containers when applying permanent make-up (PMU) and tattoos. In everyday practice, these concerns are not easy to address.

It is particularly problematic in the practice of applying permanent make-up and tattoos because these measures are so invasive. In particular, the customer's skin is pierced by the method, and blood or blood serum may issue from the treated portion of the skin. Moreover, the parts of the device that come into direct contact with the customer, in particular, the needles and needle nozzles, are contaminated by the customer's bodily fluids. In order to avoid known diseases transmitted by bodily fluids, such as AIDS and hepatitis, these parts of the device must be sterile before treatment and are to be regarded as potentially infectious after treatment. Therefore, they must be disposed of accordingly.

Thus, it is common practice that certain parts of the PMU or tattoo device, such as needles, are disposable articles. Other parts can be used several times and thus must be carefully cleaned and sterilized after use. Before use, these parts must be taken out of the sterile packaging in which they are stored and then they are mounted in or at the PMU or manual tattoo device. This requires a substantial amount of time and money and further requires great care from the users to ensure that all parts are sterile when the device is used on customers.

When applying tattoos or permanent make-up, ink to be introduced into the skin is typically taken from large ink reservoir containers, usually large ink bottles. Then the ink is either directly applied onto the customer's skin or it is injected by means of syringes, dropper pipettes or similar tools into a PMU or tattoo pen by means of which the tattoo is applied. The amount of ink in the ink bottles is significantly larger than the quantity required for one customer. One bottle is therefore used for a multitude of tattoos and make-up applications or for multiple customers.

This practice poses health risks for customers because of the danger that bodily fluids, such as blood or serum issuing from the injured skin of a customer when piercing, "carving-in" or contacting the skin while applying the ink, contact the filling aids used for transferring the ink out of the reservoir ink bottles. As a result, the bodily fluids may spread into the reservoir bottle thereby losing the sterility of the bottle. Under these circumstances, several customers can be contaminated by infectious diseases if the same ink and the same filing aid are used.

The prolonged storage of the ink in the relatively large reservoir container and the permanent extraction of small amounts for treating customers can, despite all precautionary measures, cause the contamination of the ink with dust particles, germs and bacteria and may lead to an infection in the customer. The sterility of the ink can therefore not always be reliably ensured despite careful hygienic measures. Moreover, an economic handling of the relatively expensive ink is not possible with this method.

SUMMARY OF THE INVENTION

An object of the invention is to eliminate the above-mentioned disadvantages and to reliably ensure the sterility of a device and the ink for each customer, each tattoo and each permanent make-up in a simple manner.

According to the invention, the object is solved by an ink application device for tattooing or for making permanent make-up, comprising a handle, a needle drive, a needle, a needle nozzle and a protective cap, and at least two modules releasably connected to one another, wherein one of the modules is formed as a reusable base module with an integrated needle drive, and the other module is a sterilized disposable module in which all components of the manual device capable of being infected by bodily fluids of a customer are integrated.

The ink application device is constructively divided into two or three separate modules: a basic module, a disposable or hygienic module and an optional ink module, e.g. an ink cartridge, wherein the basic module corresponds to the handle which includes the drive and is designated such that the hygienic module can be safely attached and connected to the drive.

When using a disposable module which includes all parts that can potentially be infected during treatment by the customer's bodily fluids, the exchange of single parts of the manual device, such as the needle or needle nozzles and the sterilization of the remaining parts that may have contacted the bodily fluid, becomes superfluous before the next use of the manual device on another customer. The disposable module is removed from the basic module after the treatment and is disposed of in the usual manner. Then, it is necessary for the subsequent treatment to plug a new disposable module onto the basic module to make the device ready to operate for the next customer. Since the disposable module is taken from a sterile package directly before use, its sterility is ensured without the need for special hygienic measures by the user or hygienic conditions in the treatment environment.

The connection between the basic module and the disposable module can be established and released in a simple manner so that the device can also be simply and safely used even by less experienced users.

Since the ink tank is filled before the sterilization process or after removal from the sterile packaging by means of a sterilized ink cartridge with an ink quantity sufficient for one treatment, the contamination or infection of the ink is effectively prevented, and the required sterility during treatment is ensured.

The ink quantity of approximately 0.5 to 2.0 ml provided according to preferred embodiments is usually sufficient for one tattoo or PMU. If further ink is required for larger tattoo applications, the empty ink cartridge can easily be replaced by a new, sterile cartridge without the risk of contamination or infection.

An ink container can, for instance, be used as an ink cartridge as disclosed in the German Utility Model No. 299 16 971, which is incorporated herein by reference.

A sealing diaphragm provided, according to the preferred embodiments, between the basic and disposable module ensures that no ink leaks from the ink tank of the disposable module and enters the basic module. This ensures that the reusable basic module is not exposed to bodily fluids and can be reused without having to be sterilized. In addition, the diaphragm also prevents the penetration of impurities, germs or bacteria which may adhere to the basic module, into the sterile disposable module.

The manual device according to the invention achieves the special hygienic conditions necessary for applying tattoos or PMUs with simple handling procedures to ensure sterility of the elements contacting the customer's skin.

BRIEF DESCRIPTION OF THE DRAWINGS

The above and other objects and features of the present invention will be clearly understood from the following description with respect to the preferred embodiments thereof when considered in conjunction with the accompanying drawings, in which.

DETAILED DESCRIPTION OF THE PREFERRED EMBODIMENTS

Figure 1:
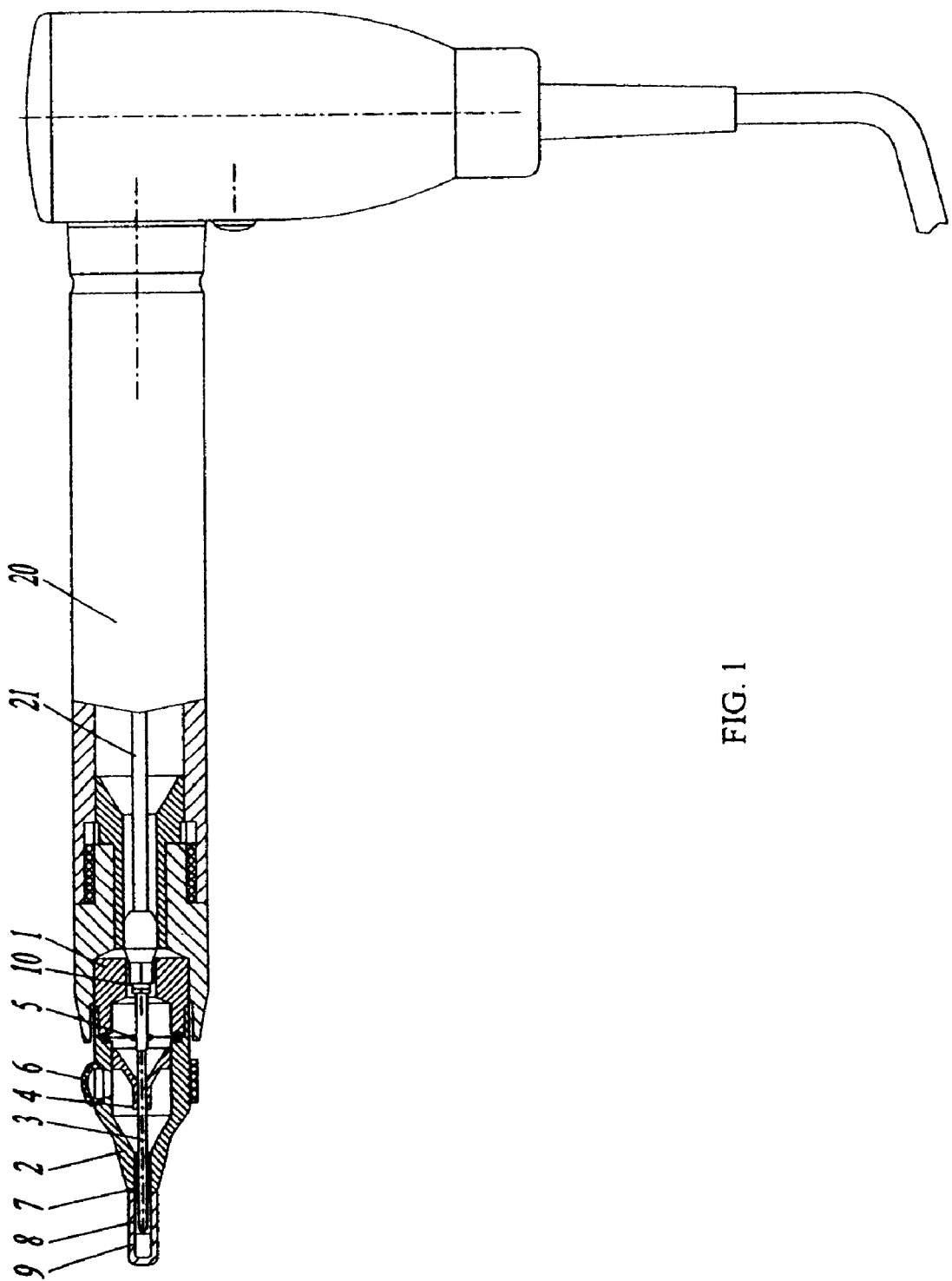
FIG. 1 shows a cross sectional view of a disposable module according to the invention which is already filled with ink and which is closed, storable and ready to operate.
Figure 2:
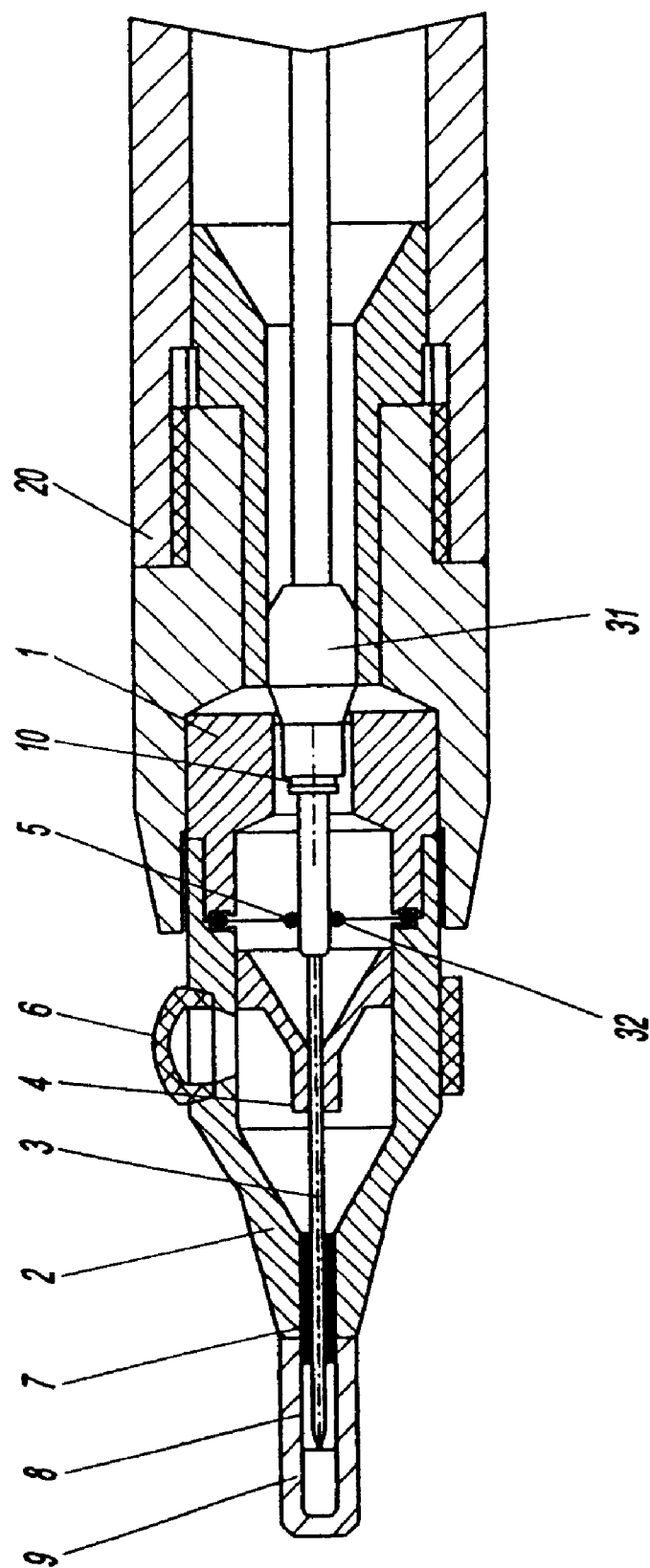
FIG. 2 shows a partial cross sectional view of the disposable module of FIG. 1.

FIGS. 1 and 2 show an embodiment of a disposable or hygienic module formed according to the invention. A basic module 20 is formed as a conventional handle. The basic module 20 comprises a drive 21 for a needle 3, which is adapted in accordance with the constructive design of a needle shaft 13.

The disposable module is provided with a housing comprising a rear housing part 1 and a front housing part 2, and a protective cap 9 which tightly locks the element towards the front when it is not in use. The disposable module of the present example is comprised of parts made of a medically compatible plastic material. In an alternative embodiment, it can also be formed as one piece. The manufacturer places the module in a sterile package, and it is suitable for long-term storage.

A thermoplastic injection needle 3 is supported within the element by a sealing and bearing element 4 and by a bearing sleeve 7. The bearing dimensions are proportioned so that simple and normal operation of the needle 3 is ensured, and the needle movement through the bearing 4 transports the ink. Moreover, the sleeve 7 ensures movement with little friction.

An ink tank 14 is closed by a collar 6 and is filled with ink. The size of the ink tank 14 preferably corresponds to an ink quantity of approximately 0.5 to 2.0 ml, since this ink quantity is usually sufficient for one treatment. Different ink quantities are of course also possible.

The ink is preferably introduced before sterilization and packaging of the disposable module, and the element is closed by the collar 6. In this manner, the sterility of the element and of the ink is ensured. The element is packaged in a storable manner. After removal from the sterile packaging, it is immediately ready to operate, and it only has to be connected to the basic module formed as a handle with the needle drive.

The leaking of ink towards the back into the basic module, which is not shown, is prevented because the bearing 4 is dimensioned to have in a tight fit, and the needle shaft 13 is closed by a diaphragm 5, that is made of a resilient material. The diaphragm 5 has a substantially centrally arranged opening for the needle 3, and the opening is provided with a sealing bead or lip 32. The sealing bead or lip 32 is disposed around the needle shaft. The resiliency of the diaphragm 5 enables movement of the needle 3 within a required stroke interval. The slidable seat of the sealing bead or lip 32 of the diaphragm 5 on the needle shaft 13 allows relief of the diaphragm in the rest position. The diaphragm 5 is preferably made of a medically compatible, rubber-like materials, which are generally known in medical technology.

A magnet 10 attached at the distal end of the needle shaft 13 secures a non-positive connection of the needle 3 with the drive (not shown) in the basic module when the disposable module is connected to the basic module. The drive is provided at the opposite end of the needle shaft 13 with a corresponding magnetic counter piece 31 to realize the magnetic coupling. The magnetic material may be soft iron or reinforced or non-reinforced sinter ceramics.

Figure 3:
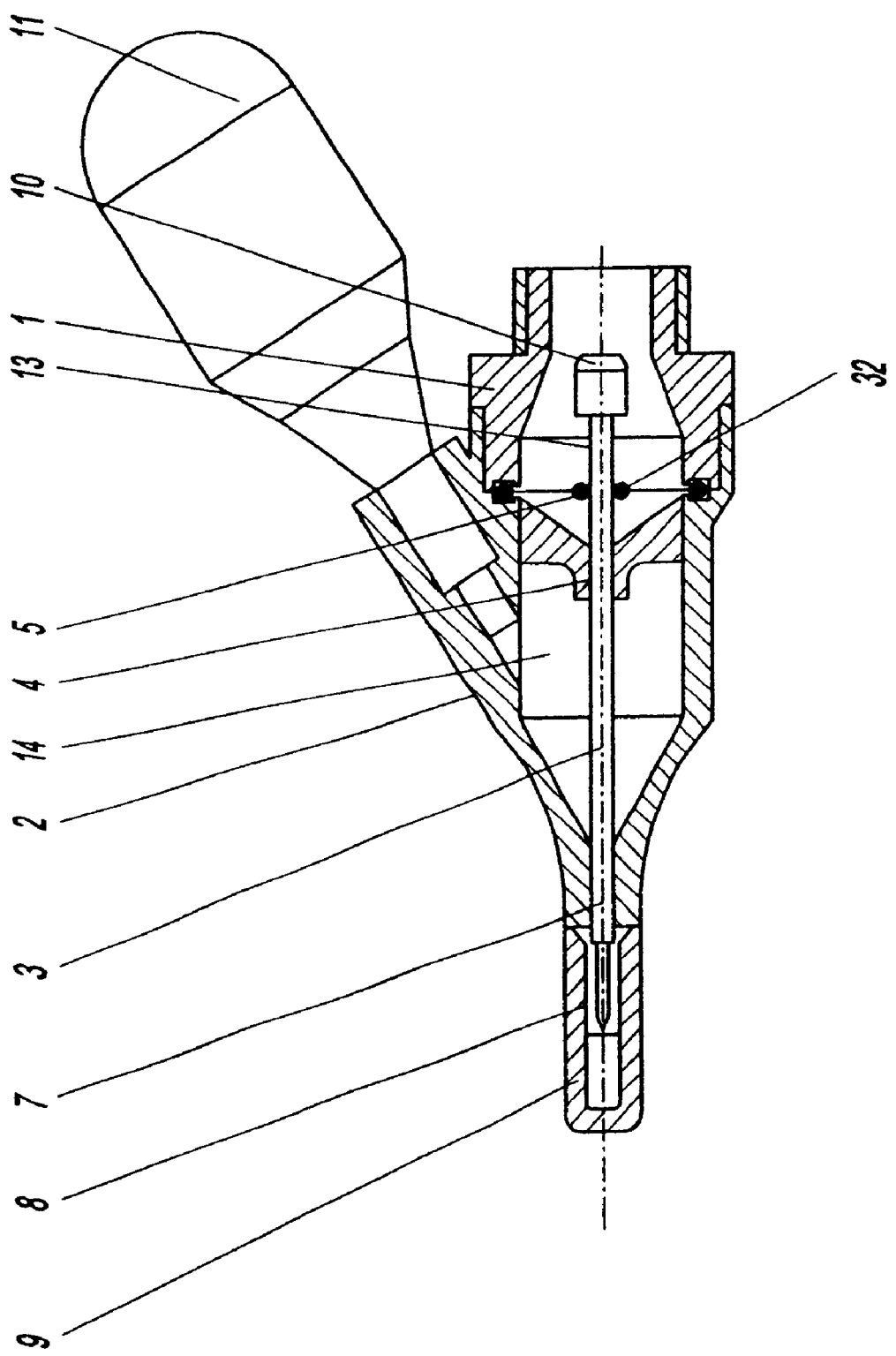
FIG. 3 shows a partial cross sectional view of an embodiment of an empty disposable module formed according to the invention with an attached ink cartridge.
Figure 4:
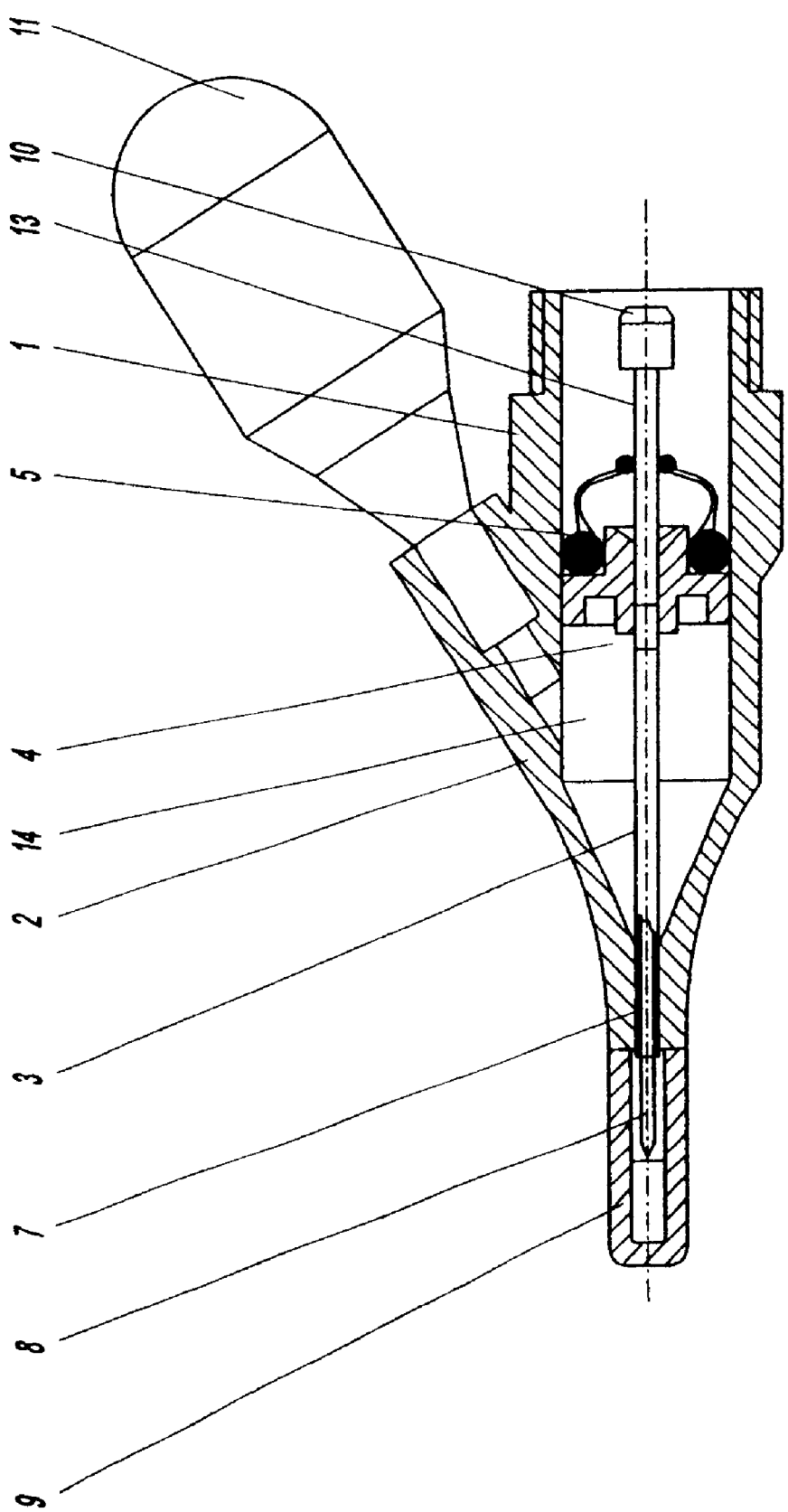
FIG. 4 shows a partial cross sectional view of another embodiment of an empty disposable module formed according to the invention.

FIGS. 3 and 4 show further embodiments of the disposable or hygienic module according to the invention. This embodiment differs from the one shown in FIGS. 1 and 2 in that the ink filling of the element is performed by plugging on a sterile ink cartridge 11. As shown in FIG. 4, a specially formed diaphragm 5 supports its resilient movement with the needle 3.

Instead of the ink cartridge 11, a micro dosing pump (not shown) can also supply the ink from a corresponding ink container into the ink tank 14. The ink is preferably discharged automatically from the ink module 11 or from the micro dosing pump into the ink tank 14. Preferably 5 to 30 ml per needle stroke are dosed. Manual operation of the ink module 11 is also possible. The ink is transported by the movement of the needle 3 through a needle nozzle 8 during operation of the manual device.

In a further embodiment, which is not shown, the needle shaft 13 can be formed cylindrically at its distal end so that it engages a clamping device provided in the basic module, preferably with a collet chuck to establish the drive connection for the needle 3.

As an alternative, the diaphragm can also be formed without an opening for the needle 3 and fully close the disposable module in the direction of the basic module. In this case, an indirect connection between the elements of the magnetic coupling with an interposed diaphragm 5 is established.

In a further embodiment, the needle shaft 13 can be formed as a pressure absorber at its distal end. The needle shaft 13 can be driven forward directly through the opening of the diaphragm 5 or indirectly through the closed diaphragm 5 by a pressure tappet not connected to the needle shaft. It can then be moved back by a return spring 12.

Figure 5:
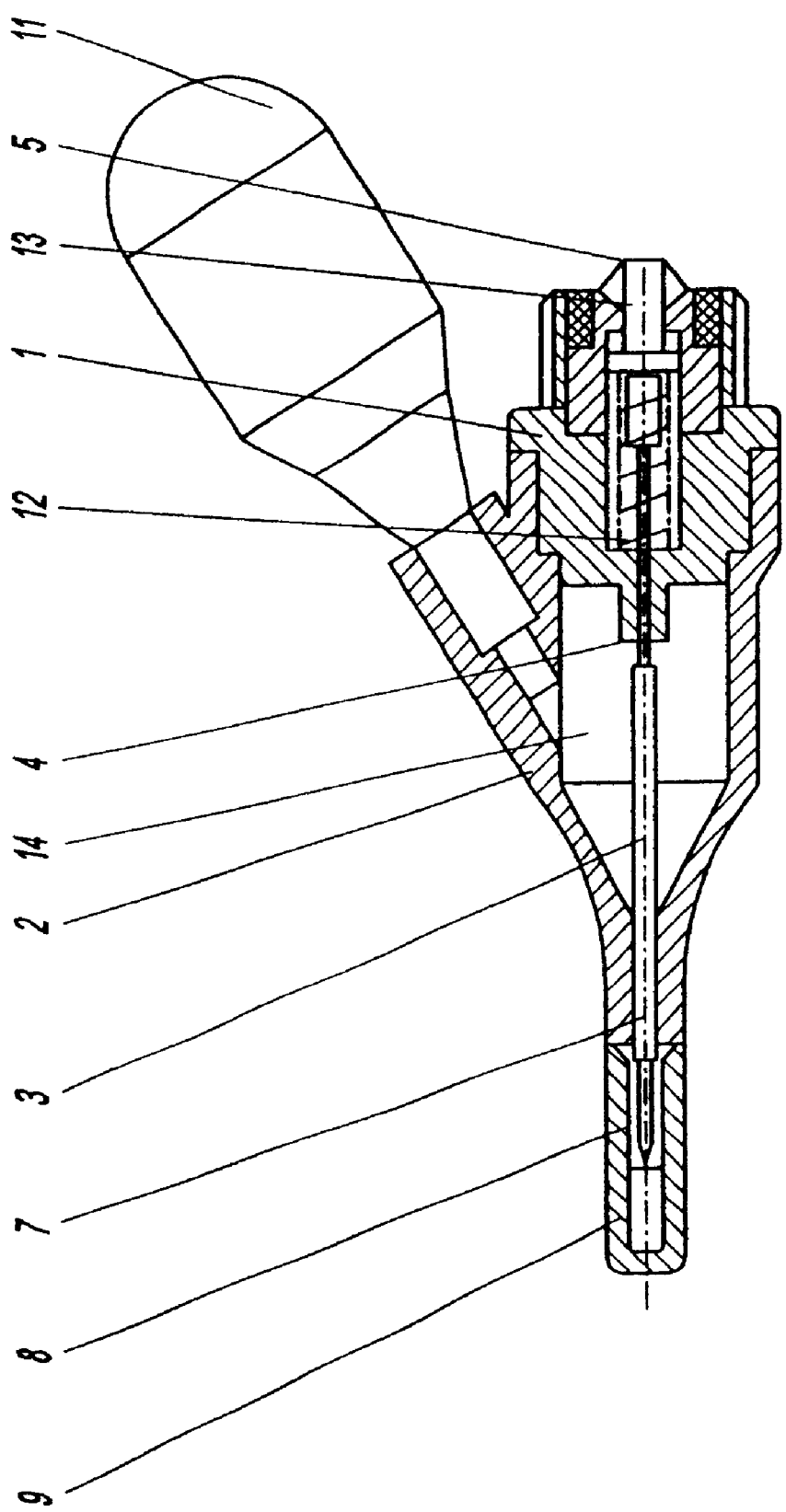
FIG. 5 shows a partial cross sectional view of yet another embodiment of an empty disposable module formed according to the invention.
Figure 6:
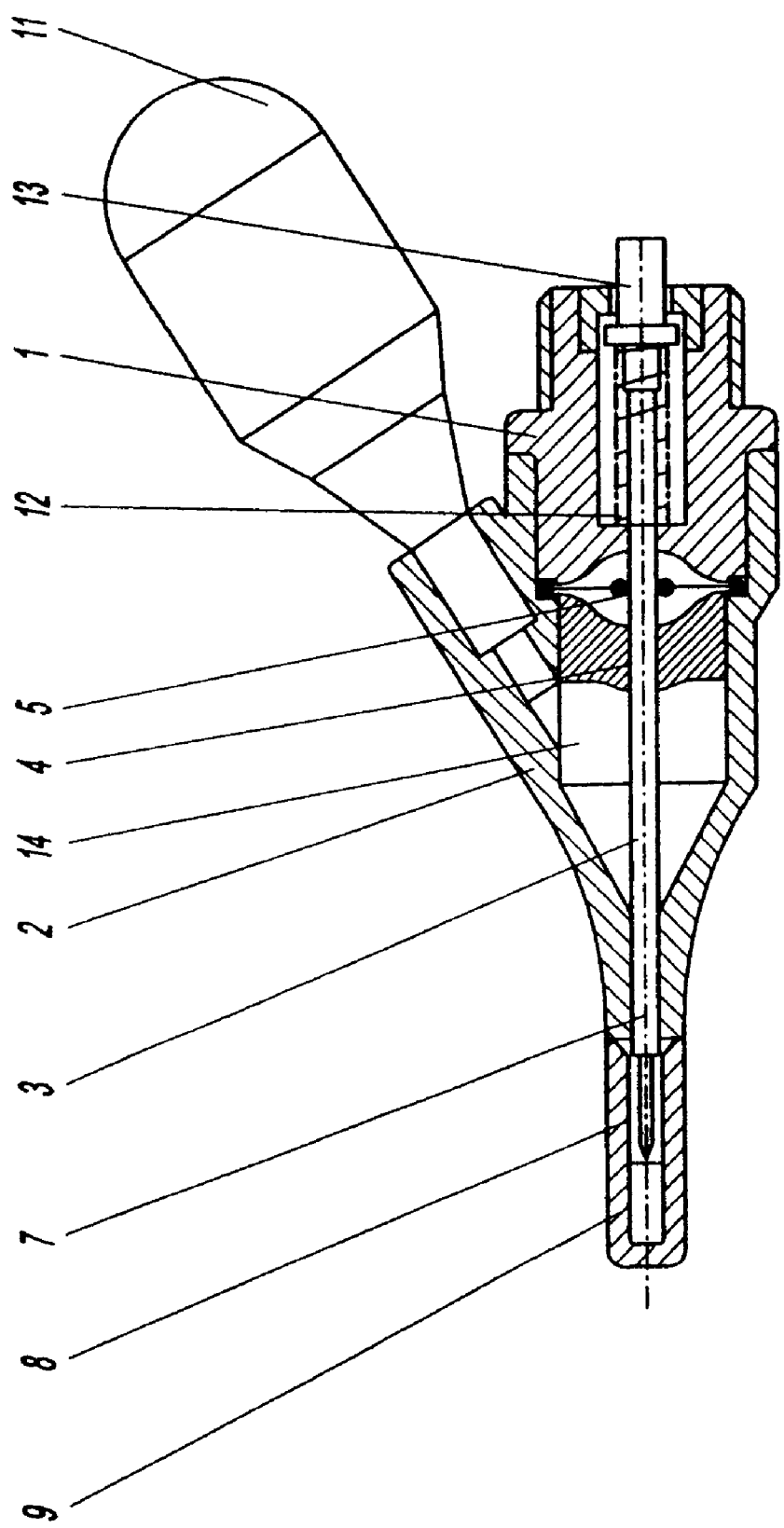
FIG. 6 shows a partial cross sectional view of a further embodiment of an empty disposable module formed according to the invention.

Further examples of embodiments of the element are shown in FIGS. 5 and 6. In both alternatives, the needles are moved by means of a return spring 12 located in a rear portion of the device. In FIG. 5, a closed form diaphragm 5 is shown, with the needle shaft 13 being formed as a pressure absorber abutting the inner side of the diaphragm that is the side facing the disposable module. On the opposite side of the diaphragm 5 (i.e. the side facing the basic module), a tappet, which is not shown, holds the needle shaft end against the force of the return spring 12 to drive the needle 3. The return movement of the needle 3 is then performed by the force of the return spring 12.

In the embodiment of FIG. 5, the disposable module is sealed in the direction of the basic module by a closed diaphragm 5. In the embodiment of FIG. 6, the diaphragm 5 is provided with an opening.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. An ink application device for tattooing or for making permanent make-up, comprising:
   a basic module having a handle and an integrated needle drive; and
   a disposable module including an outer housing substantially surrounding a needle which is supported at one end of the disposable module by a needle nozzle and which is supported at another end of the disposable module by a portion that can contact the integrated needle drive, the needle being movable relative to the outer housing, and an ink receiving portion disposed around the needle, and
   means for allowing simultaneous removal of the entire disposable module from the basic module.

2. An ink application device for tattooing or for making permanent make-up as claimed in claim 1, wherein the ink receiving portion has a volume sufficient for one application of ink.

3. An ink application device for tattooing or for making permanent make-up as claimed in claim 1, wherein the needle is disposed at least partially in said ink receiving portion so that during operation of the device, needle movement transports ink through the needle nozzle.

4. An ink application device for tattooing or for making permanent make-up as claimed in claim 1, further comprising a separate ink module attachable to an opening in the disposable module for filling the ink receiving portion, the separate ink module having a quantity of sterile ink sufficient for one application.

5. An ink application device for tattooing or for making permanent make-up as claimed in claim 4, wherein the separate ink module includes an outlet for discharging ink with each needle stroke.

6. An ink application device for tattooing or for making permanent make-up as claimed in claim 4, wherein the separate ink module includes an outlet for discharging ink into the ink receiving portion.

7. An ink application device for tattooing or for making permanent make-up as claimed in claim 1, wherein the portion that can contact the integrated needle drive is the needle shaft.

8. An ink application device for tattooing or for making permanent make-up as claimed in claim 7, wherein the needle shaft is cylindrical.

9. An ink application device for tattooing or for making permanent make-up as claimed in claim 7, further comprising a diaphragm disposed between the ink receiving portion and the basic module.

10. An ink application device for tattooing or for making permanent make-up, comprising:
    a basic module having a handle and an integrated needle drive; and
    a disposable module having a housing that includes a needle disposed therein, an ink receiving portion around the needle disposed inside the housing, a needle nozzle disposed on one end of the disposable module, another end of the disposable module having a portion that is connectable to the integrated needle drive and a bearing element disposed inside the housing and supporting the needle in the housing so that the needle, the ink receiving portion, the bearing element and the housing form a unit that is detachable from the basic module, and sealing means disposed between the ink receiving portion and the basic module for preventing liquids from reaching the basic module;
    whereby components of the device that could be infected by the bodily fluids of a user are integrated into the disposable module.

11. An ink application device for tattooing or for making permanent make-up as claimed in claim 10, wherein the ink receiving portion has a volume sufficient for one application of ink.

12. An ink application device for tattooing or for making permanent make-up as claimed in claim 10, wherein the needle is disposed at least partially in said ink receiving portion so that during operation of the device, needle movement transports ink through the needle nozzle.

13. An ink application device for tattooing or for making permanent make-up as claimed in claim 10, further comprising a separate ink module attachable to an opening in the disposable module for filling the ink receiving portion, the separate ink module having a quantity of sterile ink sufficient for one application.

14. An ink application device for tattooing or for making permanent make-up as claimed in claim 13, wherein the separate ink module includes an outlet for discharging ink with each needle stroke.

15. An ink application device for tattooing or for making permanent make-up as claimed in claim 13, wherein the separate ink module includes an outlet for discharging ink into the ink receiving portion.

16. An ink application device for tattooing or for making permanent make-up as claimed in claim 10, wherein the portion that is connectable to the integrated needle drive is the needle shaft.

17. An ink application device for tattooing or for making permanent make-up as claimed in claim 16, wherein the needle shaft is cylindrical.

18. An ink application device for tattooing or for making permanent make-up as claimed in claim 16, further comprising a diaphragm disposed between the ink receiving portion and the basic module.

19. A method of using an ink application device for tattooing or for making permanent make-up, comprising the steps of:
    providing a basic module having a handle and an integrated needle drive;
    providing a disposable module including an outer housing substantially surrounding a needle which is supported at one end of the disposable module by a needle nozzle and which is supported at another end of the disposable module by a portion that can contact the integrated needle drive, an ink receiving portion disposed around the needle, applying ink to a surface; and simultaneously removing the entire disposable module from the basic module directly following an application of ink using the ink application device.

20. The method of using an ink application device for tattooing or for making permanent make-up defined in claim 19, further comprising the step of:

replacing another disposable module on the basic module to allow another application of ink.

* * * * *

US006505530C1

(12) EX PARTE REEXAMINATION CERTIFICATE (10751st)
United States Patent
Adler et al.

(10) Number: US 6,505,530 C1
(45) Certificate Issued: *Nov. 4, 2015

(54) INK APPLICATION DEVICE FOR TATTOOING OR FOR MAKING PERMANENT MAKE-UP

(75) Inventors: Frank Adler, Berlin (DE); Walter Lisec, Berlin (DE); Gerhard Türk, Berlin (DE)

(73) Assignee: MT DERM GMBH, Berlin (DE)

Reexamination Request:
No. 90/013,371, Oct. 14, 2014

Reexamination Certificate for:
Patent No.: 6,505,530
Issued: Jan. 14, 2003
Appl. No.: 10/072,991
Filed: Feb. 12, 2002

(*) Notice: This patent is subject to a terminal disclaimer.

Related U.S. Application Data

(63) Continuation of application No. 09/671,650, filed on Sep. 28, 2000, now Pat. No. 6,345,553.

(30) Foreign Application Priority Data

Oct. 22, 1999 (DE) .............................. 299 19 199 U

(51) Int. Cl.
*B43K 5/00* (2006.01)
*A61M 37/00* (2006.01)
*A01K 11/00* (2006.01)

(52) U.S. Cl.
CPC .......... *A61M 37/0076* (2013.01); *A01K 11/005* (2013.01)

(58) Field of Classification Search
None
See application file for complete search history.

(56) References Cited

To view the complete listing of prior art documents cited during the proceeding for Reexamination Control Number 90/013,371, please refer to the USPTO's public Patent Application Information Retrieval (PAIR) system under the Display References tab.

*Primary Examiner* — Beverly M Flanagan

(57) ABSTRACT

An ink application device for tattooing or for making permanent make-up includes a handle, a needle drive, a needle, a needle nozzle and a protective cap. The device further includes at least two modules releasably connected to one another. One of the modules is formed as a reusable base module with an integrated needle drive, and the other module is a sterilized disposable module in which all components of the manual device capable of being infected by bodily fluids of a customer are integrated. The device can be constructively divided into two or three separate modules: a basic module, a disposable or hygienic module and an optional ink module. The basic module corresponds to the handle that includes the needle drive and is designed such that the hygienic module can be safely attached and connected to the integrated needle drive.

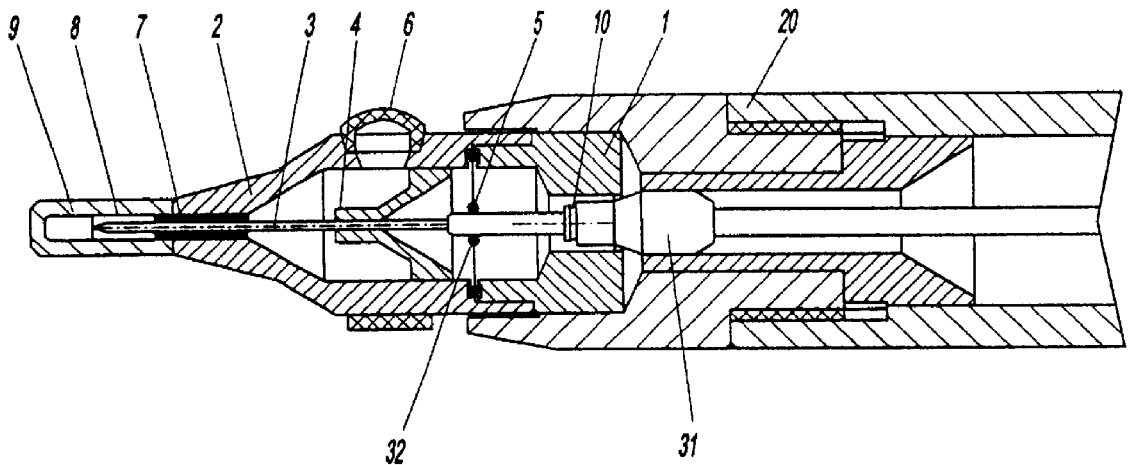

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 10, 13, 19 and 20 are determined to be patentable as amended.

Claims 2, 3, 5-9, 11, 12 and 14-18, dependent on an amended claim, are determined to be patentable.

New claims 21-101 are added and determined to be patentable.

1. An ink application device for tattooing or for making permanent make-up, comprising:
 a basic module having a handle and an integrated needle drive; and
 a *unitary sterilized* disposable module including an outer housing *and a needle, wherein the outer housing* substantially [surrounding a] *surrounds the* needle, which is supported at one end of the *unitary sterilized* disposable module by a needle nozzle and which is supported at another end of the disposable module by a portion that can contact the integrated needle drive, the needle being movable relative to the outer housing, and an ink receiving portion disposed around the needle, [and]
 means for allowing simultaneous removal of the entire *unitary sterilized* disposable module from the basic module.

4. An ink application device for tattooing or for making permanent make-up as claimed in claim 1, further comprising a separate ink module attachable to an opening in the *unitary sterilized* disposable module for filling the ink receiving portion, the separate ink module having a quantity of sterile ink sufficient for one application.

10. An ink application device for tattooing or for making permanent make-up, comprising:
 a basic module having a handle and an integrated needle drive; and
 a *unitary sterilized* disposable module having a housing that includes a needle disposed therein, an ink receiving portion around the needle disposed inside the housing, a needle nozzle disposed on one end of the *unitary sterilized* disposable module, another end of the *unitary sterilized* disposable module having a portion that is connectable to the integrated needle drive and a bearing element disposed inside the housing and supporting the needle in the housing so that the needle, the ink receiving portion, the bearing element and the housing form a *unitary* unit that is detachable from the basic module, and sealing means disposed between the ink receiving portion and the basic module for preventing liquids from reaching the basic module;
 whereby components of the device that could be infected by the bodily fluids of a user are integrated into the *unitary sterilized* disposable module.

13. An ink application device for tattooing or for making permanent make-up as claimed in claim 10, further comprising a separate ink module attachable to an opening in the *unitary sterilized* disposable module for filling the ink receiving portion, the separate ink module having a quantity of sterile ink sufficient for one application.

19. A method of using an ink application device for tattooing or for making permanent make-up, comprising the steps of:
 providing a basic module having a handle and an integrated needle drive;
 providing a *unitary sterilized* disposable module including an outer housing substantially surrounding a needle which is supported at one end of the *unitary sterilized* disposable module by a needle nozzle and which is supported at another end of the *unitary sterilized* disposable module by a portion that can contact the integrated needle drive, an ink receiving portion disposed around the needle,
 applying ink to a surface; and
 simultaneously removing the entire *unitary sterilized* disposable module from the basic module directly following an application of ink using the ink application device.

20. The method of using an ink application device for tattooing or for making permanent make-up defined in claim 19, further comprising the step of:
 replacing another *unitary sterilized* disposable module on the basic module to allow another application of ink.

*21. The method of using an ink application device for tattooing or for making permanent make-up defined in claim 19, further comprising the step of:*
 *disposing the unitary sterilized disposable module following the step of simultaneously removing the entire unitary sterilized disposable module from the basic module directly following an application of ink using the ink application device.*

*22. The method of using an ink application device for tattooing or for making permanent make-up defined in claim 19, wherein the unitary sterilized disposable module is a single unit that is taken from a sealed sterile package directly before use in the ink application device.*

*23. The method of using an ink application device for tattooing or for making permanent make-up defined in claim 19, wherein the unitary sterilized disposable module is used only once.*

*24. The method of using an ink application device for tattooing or for making permanent make-up defined in claim 19, wherein following the step of simultaneously removing the entire unitary sterilized disposable module from the basic module directly following an application of ink using the ink application device, the unitary sterilized disposable module is not re-contacted with the basic module.*

*25. An ink application device for tattooing or for making permanent make-up, comprising:*
 *a basic module having a handle and an integrated needle drive; and*
 *a unitary sterilized disposable module including an outer housing and a needle, wherein the outer housing substantially surrounds the needle, which is supported at one end of the unitary sterilized disposable module by a needle nozzle and which is supported at another end of the disposable module by a portion that can contact the integrated needle drive, the needle being movable relative to the outer housing, and an ink receiving portion disposed around the needle,*
 *means for allowing simultaneous removal of the entire unitary sterilized disposable module from the basic module, and* wherein the unitary sterilized disposable module is a single unit that is taken from a sterile package directly before use in the ink application device.

26. An ink application device for tattooing or for making permanent make-up as claimed in claim 25, wherein the ink receiving portion has a volume sufficient for one application of ink.

27. An ink application device for tattooing or for making permanent make-up as claimed in claim 25, wherein the needle is disposed at least partially in said ink receiving portion so that during operation of the device, needle movement transports ink through the needle nozzle.

28. An ink application device for tattooing or for making permanent make-up as claimed in claim 25, further comprising a separate ink module attachable to an opening in the unitary sterilized disposable module for filling the ink receiving portion, the separate ink module having a quantity of sterile ink sufficient for one application.

29. An ink application device for tattooing or for making permanent make-up as claimed in claim 28, wherein the separate ink module includes an outlet for discharging ink with each needle stroke.

30. An ink application device for tattooing or for making permanent make-up as claimed in claim 28, wherein the separate ink module includes an outlet for discharging ink into the ink receiving portion.

31. An ink application device for tattooing or for making permanent make-up as claimed in claim 25, wherein the portion that can contact the integrated needle drive is the needle shaft.

32. An ink application device for tattooing or for making permanent make-up as claimed in claim 31, wherein the needle shaft is cylindrical.

33. An ink application device for tattooing or for making permanent make-up as claimed in claim 31, further comprising a diaphragm disposed between the ink receiving portion and the basic module.

34. An ink application device for tattooing or for making permanent make-up, comprising:
   a basic module having a handle and an integrated needle drive; and
   a unitary sterilized disposable module having a housing that includes a needle disposed therein, an ink receiving portion around the needle disposed inside the housing, a needle nozzle disposed on one end of the unitary sterilized disposable module, another end of the unitary sterilized disposable module having a portion that is connectable to the integrated needle drive and a bearing element disposed inside the housing and supporting the needle in the housing so that the needle, the ink receiving portion, the bearing element and the housing form a unitary unit that is detachable from the basic module, and sealing means disposed between the ink receiving portion and the basic module for preventing liquids from reaching the basic module;
   whereby components of the device that could be infected by the bodily fluids of a user are integrated into the unitary sterilized disposable module; and
   wherein the unitary sterilized disposable module is a single unit that is taken from a sterile package directly before use in the ink application device.

35. An ink application device for tattooing or for making permanent make-up as claimed in claim 34, wherein the ink receiving portion has a volume sufficient for one application of ink.

36. An ink application device for tattooing or for making permanent make-up as claimed in claim 34, wherein the needle is disposed at least partially in said ink receiving portion so that during operation of the device, needle movement transports ink through the needle nozzle.

37. An ink application device for tattooing or for making permanent make-up as claimed in claim 34, further comprising a separate ink module attachable to an opening in the unitary sterilized disposable module for filling the ink receiving portion, the separate ink module having a quantity of sterile ink sufficient for one application.

38. An ink application device for tattooing or for making permanent make-up as claimed in claim 37, wherein the separate ink module includes an outlet for discharging ink with each needle stroke.

39. An ink application device for tattooing or for making permanent make-up as claimed in claim 37, wherein the separate ink module includes an outlet for discharging ink into the ink receiving portion.

40. An ink application device for tattooing or for making permanent make-up as claimed in claim 34, wherein the portion that is connectable to the integrated needle drive is the needle shaft.

41. An ink application device for tattooing or for making permanent make-up as claimed in claim 40, wherein the needle shaft is cylindrical.

42. An ink application device for tattooing or for making permanent make-up as claimed in claim 40, further comprising a diaphragm disposed between the ink receiving portion and the basic module.

43. A method of using an ink application device for tattooing or for making permanent make-up, comprising the steps of:
   providing a basic module having a handle and an integrated needle drive;
   providing a sealed sterile package containing a unitary sterilized disposable module including an outer housing substantially surrounding a needle which is supported at one end of the unitary sterilized disposable module by a needle nozzle and which is supported at another end of the unitary sterilized disposable module by a portion that can contact the integrated needle drive, an ink receiving portion disposed around the needle,
   applying ink to a surface; and
   simultaneously removing the entire unitary sterilized disposable module from the basic module directly following an application of ink using the ink application device.

44. The method of using an ink application device for tattooing or for making permanent make-up defined in claim 43, further comprising the step of:
   replacing another unitary sterilized disposable module on the basic module to allow another application of ink.

45. The method of using an ink application device for tattooing or for making permanent make-up defined in claim 43, further comprising the step of:
   disposing the unitary sterilized disposable module following the step of simultaneously removing the entire unitary sterilized disposable module from the basic module directly following an application of ink using the ink application device.

46. The method of using an ink application device for tattooing or for making permanent make-up defined in claim 43, wherein the unitary sterilized disposable module is a single unit that is taken from the sealed sterile package directly before use in the ink application device.

47. The method of using an ink application device for tattooing or for making permanent make-up defined in claim 43, wherein the unitary sterilized disposable module is used only once.

48. The method of using an ink application device for tattooing or for making permanent make-up defined in claim 43, wherein following the step of simultaneously removing the entire unitary sterilized disposable module from the basic module directly following an application of ink using the ink application device, the unitary sterilized disposable module is not re-contacted with the basic module.

49. An ink application device for tattooing or for making permanent make-up, comprising:
   a basic module having a handle and an integrated needle drive; and
   a sterilized disposable module assembled together as a unitary piece in a sterile package, the sterilized disposable module including a needle and an outer housing substantially surrounding the needle, which is supported at one end of the sterilized disposable module by a needle nozzle and which is supported at another end of the sterilized disposable module by a portion that can contact the integrated needle drive, the needle being movable relative to the outer housing, and an ink receiving portion disposed around the needle, and
   means for allowing simultaneous removal of the entire sterilized disposable module from the basic module.

50. An ink application device for tattooing or for making permanent make-up as claimed in claim 49, wherein the ink receiving portion has a volume sufficient for one application of ink.

51. An ink application device for tattooing or for making permanent make-up as claimed in claim 49, wherein the needle is disposed at least partially in said ink receiving portion so that during operation of the device, needle movement transports ink through the needle nozzle.

52. An ink application device for tattooing or for making permanent make-up as claimed in claim 49, further comprising a separate ink module attachable to an opening in the sterilized disposable module for filling the ink receiving portion, the separate ink module having a quantity of sterile ink sufficient for one application.

53. An ink application device for tattooing or for making permanent make-up as claimed in claim 52, wherein the separate ink module includes an outlet for discharging ink with each needle stroke.

54. An ink application device for tattooing or for making permanent make-up as claimed in claim 52, wherein the separate ink module includes an outlet for discharging ink into the ink receiving portion.

55. An ink application device for tattooing or for making permanent make-up as claimed in claim 49, wherein the portion that can contact the integrated needle drive is the needle shaft.

56. An ink application device for tattooing or for making permanent make-up as claimed in claim 55, wherein the needle shaft is cylindrical.

57. An ink application device for tattooing or for making permanent make-up as claimed in claim 55, further comprising a diaphragm disposed between the ink receiving portion and the basic module.

58. An ink application device for tattooing or for making permanent make-up, comprising:
   a basic module having a handle and an integrated needle drive; and
   a sterilized disposable module assembled together as a unitary piece in a sterile package, the sterilized disposable module having a needle and a housing that includes the needle disposed therein, an ink receiving portion around the needle disposed inside the housing, a needle nozzle disposed on one end of the disposable module, another end of the disposable module having a portion that is connectable to the integrated needle drive and a bearing element disposed inside the housing and supporting the needle in the housing so that the needle, the ink receiving portion, the bearing element and the housing form a unitary unit that is detachable from the basic module, and sealing means disposed between the ink receiving portion and the basic module for preventing liquids from reaching the basic module;
   whereby components of the device that could be infected by the bodily fluids of a user are integrated into the sterilized disposable module.

59. An ink application device for tattooing or for making permanent make-up as claimed in claim 58, wherein the ink receiving portion has a volume sufficient for one application of ink.

60. An ink application device for tattooing or for making permanent make-up as claimed in claim 58, wherein the needle is disposed at least partially in said ink receiving portion so that during operation of the device, needle movement transports ink through the needle nozzle.

61. An ink application device for tattooing or for making permanent make-up as claimed in claim 58, further comprising a separate ink module attachable to an opening in the sterilized disposable module for filling the ink receiving portion, the separate ink module having a quantity of sterile ink sufficient for one application.

62. An ink application device for tattooing or for making permanent make-up as claimed in claim 61, wherein the separate ink module includes an outlet for discharging ink with each needle stroke.

63. An ink application device for tattooing or for making permanent make-up as claimed in claim 61, wherein the separate ink module includes an outlet for discharging ink into the ink receiving portion.

64. An ink application device for tattooing or for making permanent make-up as claimed in claim 58, wherein the portion that is connectable to the integrated needle drive is the needle shaft.

65. An ink application device for tattooing or for making permanent make-up as claimed in claim 64, wherein the needle shaft is cylindrical.

66. An ink application device for tattooing or for making permanent make-up as claimed in claim 64, further comprising a diaphragm disposed between the ink receiving portion and the basic module.

67. A method of using an ink application device for tattooing or for making permanent make-up, comprising the steps of:
   providing a basic module having a handle and an integrated needle drive;
   providing a sterilized disposable module assembled together as a unitary piece in a sterile package, the sterilized disposable module including an outer housing substantially surrounding a needle which is supported at one end of the disposable module by a needle nozzle and which is supported at another end of the sterilized disposable module by a portion that can contact the integrated needle drive, an ink receiving portion disposed around the needle,
   removing the sterilized disposable module from the sterile package;
   applying ink to a surface; and simultaneously removing the entire disposable module from the basic module directly following an application of ink using the ink application device.

68. The method of using an ink application device for tattooing or for making permanent make-up defined in claim 67, further comprising the step of:
replacing another sterilized disposable module on the basic module to allow another application of ink.

69. The method of using an ink application device for tattooing or for making permanent make-up defined in claim 67, further comprising the step of:
disposing the sterilized disposable module following the step of simultaneously removing the entire sterilized disposable module from the basic module directly following an application of ink using the ink application device.

70. The method of using an ink application device for tattooing or for making permanent make-up defined in claim 67, wherein the sterilized disposable module is a single unit that is taken from the sterile package directly before use in the ink application device.

71. The method of using an ink application device for tattooing or for making permanent make-up defined in claim 67, wherein the sterilized disposable module is used only once.

72. The method of using an ink application device for tattooing or for making permanent make-up defined in claim 67, wherein following the step of simultaneously removing the entire sterilized disposable module from the basic module directly following an application of ink using the ink application device, the sterilized disposable module is not recontacted with the basic module.

73. An ink application device for tattooing or for making permanent make-up, comprising:
a basic module having a handle and an integrated needle drive; and
a sterilized disposable module assembled together as a unitary piece, the sterilized disposable module including a needle and an outer housing substantially surrounding the needle, which is supported at one end of the sterilized disposable module by a needle nozzle and which is supported at another end of the sterilized disposable module by a portion that can contact the integrated needle drive, the needle being movable relative to the outer housing, and an ink receiving portion disposed around the needle,
a sealed sterile package housing the sterilized disposable module, and
means for allowing simultaneous removal of the entire disposable module from the basic module.

74. An ink application device for tattooing or for making permanent make-up as claimed in claim 73, wherein the ink receiving portion has a volume sufficient for one application of ink.

75. An ink application device for tattooing or for making permanent make-up as claimed in claim 73, wherein the needle is disposed at least partially in said ink receiving portion so that during operation of the device, needle movement transports ink through the needle nozzle.

76. An ink application device for tattooing or for making permanent make-up as claimed in claim 73, further comprising a separate ink module attachable to an opening in the sterilized disposable module for filling the ink receiving portion, the separate ink module having a quantity of sterile ink sufficient for one application.

77. An ink application device for tattooing or for making permanent make-up as claimed in claim 76, wherein the separate ink module includes an outlet for discharging ink with each needle stroke.

78. An ink application device for tattooing or for making permanent make-up as claimed in claim 76, wherein the separate ink module includes an outlet for discharging ink into the ink receiving portion.

79. An ink application device for tattooing or for making permanent make-up as claimed in claim 73, wherein the portion that can contact the integrated needle drive is the needle shaft.

80. An ink application device for tattooing or for making permanent make-up as claimed in claim 79, wherein the needle shaft is cylindrical.

81. An ink application device for tattooing or for making permanent make-up as claimed in claim 79, further comprising a diaphragm disposed between the ink receiving portion and the basic module.

82. An ink application device for tattooing or for making permanent make-up, comprising:
a basic module having a handle and an integrated needle drive; and
a sterilized disposable module assembled together as a unitary piece, the sterilized disposable module having a needle and a housing that includes the needle disposed therein, an ink receiving portion around the needle disposed inside the housing, a needle nozzle disposed on one end of the sterilized disposable module, another end of the sterilized disposable module having a portion that is connectable to the integrated needle drive and a bearing element disposed inside the housing and supporting the needle in the housing so that the needle, the ink receiving portion, the bearing element and the housing form a unit that is detachable from the basic module, and sealing means disposed between the ink receiving portion and the basic module for preventing liquids from reaching the basic module; and
a sealed sterile package housing the sterilized disposable module;
whereby components of the device that could be infected by the bodily fluids of a user are integrated into the disposable module.

83. An ink application device for tattooing or for making permanent make-up as claimed in claim 82, wherein the ink receiving portion has a volume sufficient for one application of ink.

84. An ink application device for tattooing or for making permanent make-up as claimed in claim 82, wherein the needle is disposed at least partially in said ink receiving portion so that during operation of the device, needle movement transports ink through the needle nozzle.

85. An ink application device for tattooing or for making permanent make-up as claimed in claim 82, further comprising a separate ink module attachable to an opening in the sterilized disposable module for filling the ink receiving portion, the separate ink module having a quantity of sterile ink sufficient for one application.

86. An ink application device for tattooing or for making permanent make-up as claimed in claim 85, wherein the separate ink module includes an outlet for discharging ink with each needle stroke.

87. An ink application device for tattooing or for making permanent make-up as claimed in claim 85, wherein the separate ink module includes an outlet for discharging ink into the ink receiving portion.

88. An ink application device for tattooing or for making permanent make-up as claimed in claim 82, wherein the portion that is connectable to the integrated needle drive is the needle shaft.

89. An ink application device for tattooing or for making permanent make-up as claimed in claim 88, wherein the needle shaft is cylindrical.

90. An ink application device for tattooing or for making permanent make-up as claimed in claim 88, further comprising a diaphragm disposed between the ink receiving portion and the basic module.

91. An ink application device for tattooing or for making permanent make-up as claimed in claim 1, wherein the unitary sterilized disposable module comprises a diaphragm that fully closes the unitary sterilized disposable module in the direction of the basic module.

92. An ink application device for tattooing or for making permanent make-up as claimed in claim 10, wherein the unitary sterilized disposable module comprises a diaphragm that fully closes the unitary sterilized disposable module in the direction of the basic module.

93. The method of using an ink application device for tattooing or for making permanent make-up as recited in claim 19, wherein the unitary sterilized disposable module comprises a diaphragm that fully closes the unitary sterilized disposable module in the direction of the basic module.

94. An ink application device for tattooing or for making permanent make-up as claimed in claim 25, wherein the unitary sterilized disposable module comprises a diaphragm that fully closes the unitary sterilized disposable module in the direction of the basic module.

95. An ink application device for tattooing or for making permanent make-up as claimed in claim 34, wherein the unitary sterilized disposable module comprises a diaphragm that fully closes the unitary sterilized disposable module in the direction of the basic module.

96. The method of using an ink application device for tattooing or for making permanent make-up as claimed in claim 43, wherein the unitary sterilized disposable module comprises a diaphragm that fully closes the unitary sterilized disposable module in the direction of the basic module.

97. An ink application device for tattooing or for making permanent make-up as claimed in claim 49, wherein the sterilized disposable module comprises a diaphragm that fully closes the sterilized disposable module in the direction of the basic module.

98. An ink application device for tattooing or for making permanent make-up as claimed in claim 58, wherein the sterilized disposable module comprises a diaphragm that fully closes the sterilized disposable module in the direction of the basic module.

99. The method of using an ink application device for tattooing or for making permanent make-up as claimed in claim 67, wherein the sterilized disposable module comprises a diaphragm that fully closes the sterilized disposable module in the direction of the basic module.

100. An ink application device for tattooing or for making permanent make-up as claimed in claim 73, wherein the sterilized disposable module comprises a diaphragm that fully closes the sterilized disposable module in the direction of the basic module.

101. An ink application device for tattooing or for making permanent make-up as claimed in claim 82, wherein the sterilized disposable module comprises a diaphragm that fully closes the sterilized disposable module in the direction of the basic module.

\* \* \* \* \*